US008568996B2

(12) United States Patent
Enghild et al.

(10) Patent No.: US 8,568,996 B2
(45) Date of Patent: Oct. 29, 2013

(54) MMP ACTIVATION PEPTIDE DETECTION IN BIOLOGICAL SAMPLES

(75) Inventors: Jan Johannes Enghild, Aarhus (DK); Naftali Kaminski, Pittsburgh, PA (US); Tim D. Oury, Wexford, PA (US); Laura Voeghtly, Tarentum, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 341 days.

(21) Appl. No.: 13/121,142

(22) PCT Filed: Oct. 2, 2009

(86) PCT No.: PCT/US2009/059388
§ 371 (c)(1),
(2), (4) Date: May 19, 2011

(87) PCT Pub. No.: WO2010/047938
PCT Pub. Date: Apr. 29, 2010

(65) Prior Publication Data
US 2011/0212473 A1    Sep. 1, 2011

Related U.S. Application Data

(60) Provisional application No. 61/107,188, filed on Oct. 21, 2008.

(51) Int. Cl.
*G01N 31/00*    (2006.01)
*G01N 33/53*    (2006.01)

(52) U.S. Cl.
USPC ........... 435/7.21; 435/7.1; 436/501; 436/518; 422/430; 530/300; 530/350

(58) Field of Classification Search
None
See application file for complete search history.

(56) References Cited

U.S. PATENT DOCUMENTS 6,300,088 B1    10/2001 Enghild et al.

FOREIGN PATENT DOCUMENTS

WO        0188544 A2    11/2001
WO    2010028274 A1    3/2010

OTHER PUBLICATIONS

Collard et al. Acute Exacerbations of Idiopathic Pulmonary Fibrosis. Am. J Respir. Crit. Care Med. 2007, 176: 636-43.
Corbel et al. Inhibition of bleomycin-induced pulmonary fibrosis in mice by the matrix metalloproteinase inhibitor batimastat. J. Pathol. 2001,193: 538-545.
Coultas et al. The Epidemiology of Interstitial Lung Diseases. Am. J. Respir. Crit. Care Med. 1994, 150: 967-972.
Fattman et al. Increased sensitivity to asbestos-induced lung injury in mice lacking extracellular superoxide dismutase. Free Radical Biology and Medicine 2006, 40: 601-607.
Garcia-Alvarez et al. Membrane type-matrix metalloproteinases in idiopathic pulmonary fibrosis. *Sarcoidosis vasculitis* Diffuse Lung Diseases 2006, 23: 13-21.
Gills et al. Nelfinavir, A Lead HIV Protease Inhibitor, Is a Broad-Spectrum, Anticancer Agent that Induces Endoplasmic Reticulum Stress, Autophagy, and Apoptosis in vitro and in vivo. Clinical Cancer Research 2007, 13(17): 5183-5194.
Hanemaaijer et al. MMP-9 Activity in Urine from Patients with Various Tumors, as Measured by a Novel MMP Activity Assay Using Modified Urokinase as a Substrate. Annals New York Academy of Sciences 1999, 878: 141-49.
Henry et al. Matrix metalloproteinases and tissue inhibitor of metalloproteinase-1 in sarcoidosis and IPF. European Respiratory Journal 2002, 20: 1220-1227.
Ihaka et al. A Language for Data Analysis and Graphics. Journal of Computational and Graphical Statistics Sep. 1996, 5(3): 299-314.
Lagente et al. Role of matrix metalloproteinases in the development of airway inflammation and remodeling. Brazilian Journal of Medical and Biological Research 2005, 38: 1521-30.
Meltzer et al. Idiopathic pulmonary fibrosis. Orphanet Journal of Rare Diseases Mar. 26, 2008, 3: 8, 15 pages.
Pyrko et al. HIV-I Protease Inhibitors Nelfinavir and Atazanavir Induce Malignant Glioma Death by Triggering Endoplasmic Reticulum Stress. Cancer Research 2007, 67: 10920-10928.
Raghu et al. Incidence and Prevalence of Idiopathic Pulmonary Fibrosis. Am. J. Respir. Crit. Care Med. 2006, 174: 810-16.
Rosas et al. MMP1 and MMP7 as Potential Peripheral Blood Biomarkers in Idiopathic Pulmonary Fibrosis. PLoS Medicine Apr. 2008, 5(4): e93, 0623-33.
Selman et al. Idiopathic Pulmonary Fibrosis: Prevailing and Evolving Hypotheses about Its Pathogenesis and Implications for Therapy. Ann. Intern. Med. 2001, 134: 136-51.
Selman et al. Idiopathic Pulmonary Fibrosis: Pathogenesis and Therapeutic Approaches. Drugs 2004, 64(4): 405-430.
Selman et al. Accelerated Variant of Idiopathic Pulmonary Fibrosis: Clinical Behavior and Gene Expression Pattern. PLoS One May 2007, 2(5): e482, 1-11.
Siddiqui. Review of Rapid disease progression is an important cause of death in IPF. (Martinez et al. Ann. Intern. Med. 2005, 142:963-8) Thorax 2005, 60: 833.
Suga et al. Characteristic Elevation of Matrix Metalloproteinase Activity in Idiopathic Interstitial Pneumonias. Am. J. Respir. Crit. Care Med. 2000, 162: 1949-1956.
Tan et al. Matrix Metalloproteinases Promote Inflammation and Fibrosis in Asbestos-Induced Lung Injury in Mice. Am. J. Respir. Cell Mol. Biol. 2006, 35: 289-297.
Visse et al. Matrix Metalloproteinases and Tissue Inhibitors of Metalloproteinases: Structure, Function, and Biochemistry. Circulation Research 2003, 92: 827-839.
Voeghtly et al. Potential Clinical Importance of the Activation Peptide of Prostate-specific Antigen. Int. J. Clin. Exp. Pathol. 2009, 2: 588-598.
Zuo et al. Gene expression analysis reveals matrilysin as a key regulator of pulmonary fibrosis in mice and humans. PNAS Apr. 30, 2002, 99(9): 6292-6297.

*Primary Examiner* — Lisa Cook
(74) *Attorney, Agent, or Firm* — The Webb Law Firm

(57) ABSTRACT

A method is provided along with related reagent kits for aiding the diagnosis of IPF or other interstitial lung diseases, as well as for potential monitoring of disease progression or therapeutic response to treatment.

22 Claims, 8 Drawing Sheets

```
            1          11         21         31         41         51
   1 MEALMARGAL TGPLRALCLL GCLLSHAAAA PSPIIKFPGD VAPKTDKELA VQYLNTFYGC   60
  61 PKESCNLFVL KDTLKKMQKF FGLPQTGDLD QNTIETMRKP RCGNPDVANY NFFPRKPKWD  120
 121 KNQITYRIIG YTPDLDPETV DDAFARAFQV WSDVTPLRFS RIHDGEADIM INFGRWEHGD  180
 181 GYPFDGKDGL LAHAFAPGTG VGGDSHFDDD ELWTLGEGQV VRVKYGNADG EYCKFPFLFN  240
 241 GKEYNSCTDT GRSDGFLWCS TTYNFEKDGK YGFCPHEALF TMGGNAEGQP CKFPFRFQGT  300
 301 SYDSCTTEGR TDGYRWCGTT EDYDRDKKYG FCPETAMSTV GGNSEGAPCV FPFTFLGNKY  360
 361 ESCTSAGRSD GKMWCATTAN YDDDRKWGFC PDQGYSLFLV AAHEFGHAMG LEHSQDPGAL  420
 421 MAPIYTYTKN FRLSQDDIKG IQELYGASPD IDLGTGPTPT LGPVTPEICK QDIVFDGIAQ  480
 481 IRGEIFFFKD RFIWRTVTPR DKPMGPLLVA TFWPELPEKI DAVYEAPQEE KAVFFAGNEY  540
 541 WIYSASTLER GYPKPLTSLG LPPDVQRVDA AFNWSKNKKT YIFAGDKFWR YNEVKKKMDP  600
 601 GFPKLIADAW NAIPDNLDAV VDLQGGGHSY FFKGAYYLKL ENQSLKSVKF GSIKSDWLGC
```

Fig. 1

```
            1          11         21         31         41         51
   1 MRLTVLCAVC LLPGSLALPL PQEAGGMSEL QWEQAQDYLK RFYLYDSETK NANSLEAKLK   60
  61 EMQKFFGLPI TGMLNSRVIE IMQKPRCGVP DVAEYSLFPN SPKWTSKVVT YRIVSYTRDL  120
 121 PHITVDRLVS KALNMWGKEI PLHFRKVVWG TADIMIGFAR GAHGDSYPFD GPGNTLAHAF  180
 181 APGTGLGGDA HFDEDERWTD GSSLGINFLY AATHELGHSL GMGHSSDPNA VMYPTYGNGD  240
 241 PQNFKLSQDD IKGIQKLYGK RSNSRKK
```

Fig. 2

```
            1          11         21         31         41         51
   1 MFSLKTLPFL LLLHVQISKA FPVSSKEKNT KTVQDYLEKF YQLPSNQYQS TRKNGTNVIV   60
  61 EKLKEMQRFF GLNVTGKPNE ETLDMMKKPR CGVPDSGGFM LTPGNPKWER TNLTYRIRNY  120
 121 TPQLSEAEVE RAIKDAFELW SVASPLIFTR ISQGEADINI AFYQRDHGDN SPFDGPNGIL  180
 181 AHAFQPGQGI GGDAHFDAEE TWTNTSANYN LFLVAAHEFG HSLGLAHSSD PGALMYPNYA  240
 241 FRETSNYSLP QDDIDGIQAI YGLSSNPIQP TGPSTPKPCD PSLTFDAITT LRGEILFFKD  300
 301 RYFWRRHPQL QRVEMNFISL FWPSLPTGIQ AAYEDFDRDL IFLFKGNQYW ALSGYDILQG  360
 361 YPKDISNYGF PSSVQAIDAA VFYRSKTYFF VNDQFWRYDN QRQFMEPGYP KSISGAFPGI  420
 421 ESKVDAVFQQ EHFFHVFSGP RYYAFDLIAQ RVTRVARGNK WLNCRYG
```

Fig. 3

```
           1          11         21         31         41         51
   1 MSLWQPLVLV LLVLGCCFAA PRQRQSTLVL FPGDLRTNLT DRQLAEEYLY RYGYTRVAEM    60
  61 RGESKSLGPA LLLLQKQLSL PETGELDSAT LKAMRTPRCG VPDLGRFQTF EGDLKWHHHN   120
 121 ITYWIQNYSE DLPRAVIDDA FARAFALWSA VTPLTFTRVY SRDADIVIQF GVAEHGDGYP   180
 181 FDGKDGLLAH AFPPGPGIQG DAHFDDDELW SLGKGVVVPT RFGNADGAAC HFPFIFEGRS   240
 241 YSACTTDGRS DGLPWCSTTA NYDTDDRFGF CPSERLYTQD GNADGKPCQF PFIFQGQSYS   300
 301 ACTTDGRSDG YRWCATTANY DRDKLFGFCP TRADSTVMGG NSAGELCVFP FTFLGKEYST   360
 361 CTSEGRGDGR LWCATTSNFD SDKKWGFCPD QGYSLFLVAA HEFGHALGLD HSSVPEALMY   420
 421 PMYRFTEGPP LHKDDVNGIR HLYGPRPEPE PRPPTTTTPQ PTAPPTVCPT GPPTVHPSER   480
 481 PTAGPTGPPS AGPTGPPTAG PSTATTVPLS PVDDACNVNI FDAIAEIGNQ LYLFKDGKYW   540
 541 RFSEGRGSRP QGPFLIADKW PALPRKLDSV FEEPLSKKLF FFSGRQVWVY TGASVLGPRR   600
 601 LDKLGLGADV AQVTGALRSG RGKMLLFSGR RLWRFDVKAQ MVDPRSASEV DRMFPGVPLD   660
 661 THDVFQYREK AYFCQDRFYW RVSSRSELNQ VDQVGYVTYD ILQCPED
```

*Fig. 4*

MMP ACTIVATION PEPTIDE DETECTION IN BIOLOGICAL SAMPLES

CROSS REFERENCE TO RELATED APPLICATIONS

This application is a National Stage of International Application No. PCT/US2009/059388, filed Oct. 2, 2009, which in turn claims the benefit of U.S. Provisional Patent Application No. 61/107,188, filed Oct. 21, 2008, which is incorporated herein by reference in its entirety.

STATEMENT REGARDING FEDERAL FUNDING

This invention was made with government support under the National Institutes of Health Grant Nos. R01 HL63700 and R21ES01386. The government has certain rights in this invention.

Idiopathic pulmonary fibrosis (IPF) is a chronic interstitial lung disease of unknown etiology. IPF is a progressive life threatening disease that is characterized as excessive deposition of fibrotic tissue in the interstitium with minimal associated inflammation. The incidence of IPF is 29/100,000 in the general population and the median survival rate for individuals diagnosed with IPF is between 3 to 5 years. There is currently no cure or significant treatment for this disease and no effective method to monitor progression in IPF patients. Historically IPF has been seen as a gradually progressive disease. However, some patients with IPF experience a rapid deterioration of lung function and accelerated death. These episodes have been termed acute exacerbations of IPF.

Matrix metalloproteases (MMPs) are a family of at least 25 proteases that regulate extracellular matrix turnover. Several studies have shown that MMP activation contributes to the pathogenesis of pulmonary fibrosis in animal models (Corbel M, et al., *J Pathol* 193: 538-545, 2001; Tan R J, et al. *Am J Respir Cell Mol Biol* 35: 289-297, 2006; and Zuo F, et al. *Proc Natl Acad Sci USA* 99: 6292-6297, 2002). Also, there are many studies that have found increased MMP expression and activation in human IPF lungs (Zuo F, et al. *Proc Natl Acad Sci USA* 99: 6292-6297, 2002; Henry M T, et al. *Eur Respir J* 20: 1220-1227, 2002; Suga M, et al. *Am J Respir Crit. Care Med* 162: 1949-1956, 2000; Rosas I O, et al. *PLoS Med* 5: e93, 2008; and Garcia-Alvarez J, et al. *Sarcoidosis Vasc Diffuse Lung Dis* 23: 13-21, 2006)(6-10). Most MMPs including MMP2, MMP7, MMP8, and MMP9 are secreted as pro-enzymes with a signal sequence and pro peptide of about 80 amino acids that gets cleaved extracellularly upon activation. All members of the MMP family share a common catalytic core with a $Zn^{2+}$ in its active site. The pro peptide domain contains a sequence (PRCGxPD) termed the cysteine switch which contains a conserved cysteine that is involved in chelating the active $Zn^{2+}$ site. Full MMP activation is brought about by disruption of the cysteine-zinc interaction and removal of the pro peptide (Visse R, et al. *Circ Res* 92: 827-839, 2003).

Activated MMPs react rapidly with protease inhibitors including tissue inhibitor of metalloproteinases (TIMPS) and $\alpha_2$-macroglobulin in the blood. These protein complexes are removed from the circulatory system by hepatocyte-mediated endocytosis. This rapid clearance likely interferes with detection of the active MMP proteins in the urine or bloodstream resulting in the inability to accurately detect the total amount of MMP activation occurring simply by measuring the steady state amount in biological fluids.

SUMMARY

Activation peptide concentration in urine is shown herein to be representative of total protease activation. Therefore detection of the activation peptides for MMPs will give a more accurate representation of MMP activation due to their simple renal clearance as opposed to the complex clearance mechanisms of the full length active MMPs. Because MMP activation contributes to disease initiation and progression, we feel that the accurate detection of activation of these proteases will be relevant clinically and may allow for earlier detection and/or following progression of lung injury associated, for example, with IPF and other diseases, such as HP (Hypersensitivity Pneumonitis), NSIP (Nonspecific Interstitial Pneumonia), COPD (Chronic Obstructive Pulmonary Disease), and sarcoidosis, in which lung injury occurs and MMP activation is observed.

Our experiments show that the activation peptides of MMPs are detectable in the urine via immunoassay (ELISA) in mice with lung injury (lung fibrosis) and human patients with IPF, and are at elevated levels compared to what is found in the urine of controls without pulmonary fibrosis. These data indicate that urine detection of MMP activation peptides is feasible and correlates with disease. Because MMP activation contributes to disease initiation and progression, accurate detection of activation of these proteases will be relevant clinically and should allow for earlier detection of disease as well as allow for prediction of acute exacerbations.

Thus provided is a method of identifying interstitial lung disease, monitoring interstitial lung disease progression, or determining effectiveness of treatment of an interstitial lung disease in a patient. The method comprises determining a level of one or more of MMP2 activation peptide, MMP7 activation peptide, MMP8 activation peptide and MMP9 activation peptide in urine of the patient, and identifying whether the patient has interstitial lung disease by determining if levels of one or more of MMP2 activation peptide, MMP7 activation peptide, MMP8 activation peptide and MMP9 activation peptide in urine of the patient exceed a threshold level indicative of interstitial lung disease. A kit also is provided, which comprises reagents useful in the methods described herein.

The methods described herein have significant advantages over methods that analyze MMP concentration in blood or BAL (bronchoalveolar lavage). Biological detection of the full-length protein can be altered based on confounding factors such as receptor mediated proteinase clearance. MMP activation peptide detection as described herein is not altered by these factors as the activation peptides are cleared through simple renal filtration as opposed to receptor mediated endocytosis. Also, detection of MMP activation peptides in the urine is less invasive, and often a cheaper sampling method.

BRIEF DESCRIPTION OF THE DRAWINGS

FIG. 1 provides a sequence of human MMP2 (UniProtKB/Swiss-Prot: P08253 (SEQ ID NO: 1, with bases 30-109 (bold) representing the MMP2 activation peptide for this sequence).

FIG. 2 provides a sequence of human MMP7 (UniProtKB/Swiss-Prot: P09237 (SEQ ID NO: 2, with bases 18-94 (bold) representing the MMP7 activation peptide for this sequence).

FIG. 3 provides a sequence of human MMP8 (UniProtKB/Swiss-Prot: P22894 (SEQ ID NO: 3, with bases 21-100 (bold) representing the MMP8 activation peptide for this sequence).

FIG. 4 provides a sequence of human MMP9 (UniProtKB/Swiss-Prot: P14780 (SEQ ID NO: 4, with bases 20-93 (bold) representing the MMP9 activation peptide for this sequence).

(FIG. 7A) The relative concentration of MMP2, MMP7, and MMP9 activation peptides are significantly higher in the urine of IPF patients (n=42) compared to the urine of healthy age matched controls (n=30) as detected by ELISA. (FIG. 7B) A classification tree obtained by CART when applied to relative urine MMP activation peptide concentration from IPF patients and controls shows that these markers can be used as classifiers to correctly identify IPF patients from controls. All data are presented as control/IPF and are based on urine MMP activation peptide levels divided by urine creatinine levels (μg/ml). (FIG. 7C) ROC curves for using each of the four markers, or their combination, to classify samples as IPF or control. Sensitivity, or true positive rate, is potted on the y-axis, and false positive rate, or 1—specificity, is plotted on the x-axis. The area under each ROC curve is equal to the numerator of the Mann-Whitney U-statistic comparing the marker distributions between IPF and control samples.

DETAILED DESCRIPTION

Figure 5:
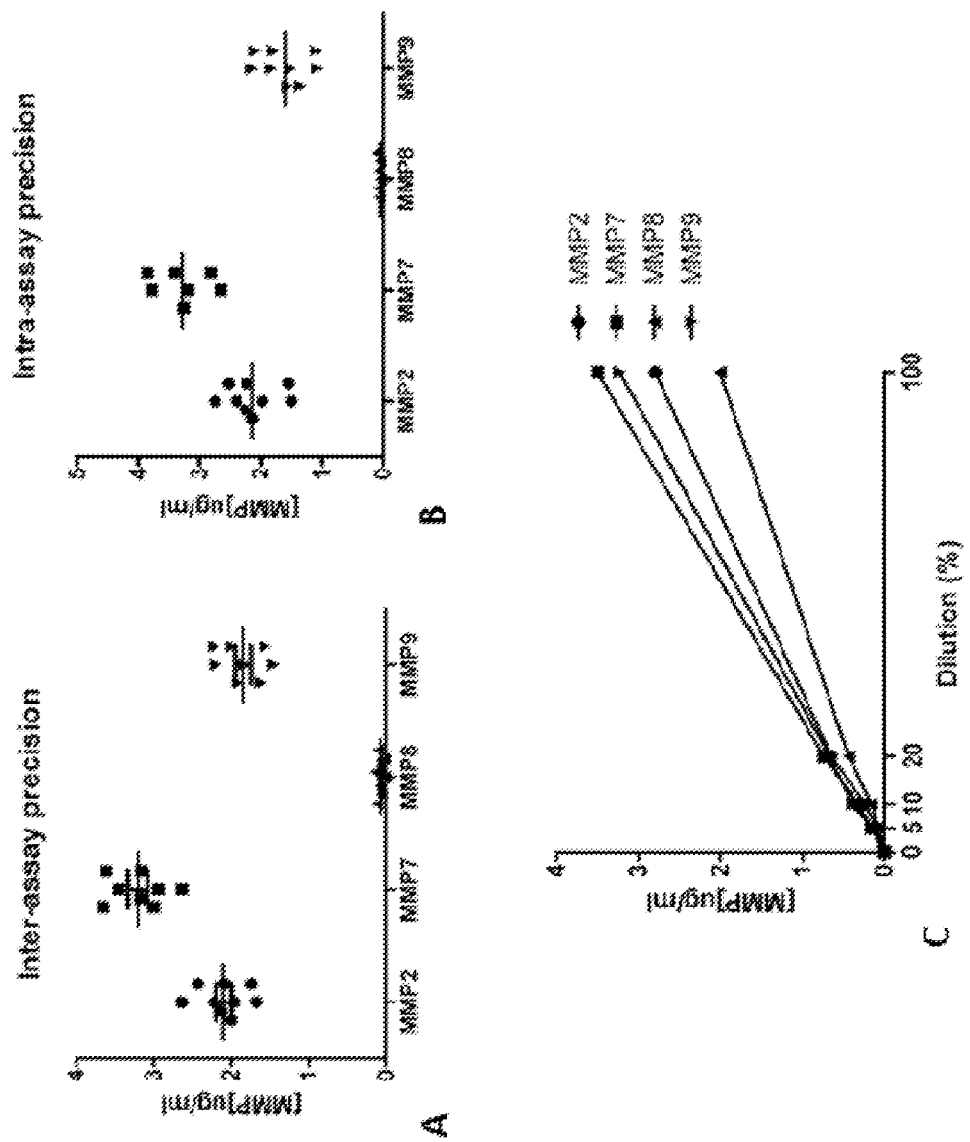
FIG. 5. Each of the MMP Activation Peptide ELISAs Were Independently Validated. Validation profiles of MMP activation peptide ELISAs. When determining precision, each of the assays had a coefficient of variance less than 10% in both the (A) inter-assay test and the (B) intra-assay test. (C) All four MMP activation peptide assays shared dilution linearity.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values.

As used herein, the term "patient" refers to members of the animal kingdom including but not limited to mammals and human beings and is not limited to humans or animals in a doctor-patient or veterinarian-patient relationship.

"Interstitial Lung Disease" (also known as diffuse parenchymal lung disease) is a group of lung disorders which result in scarring and dysfunction of the alveolus (air sac) in the lung. Symptoms of interstitial lung disease typically arise secondary to fibrosis of the lung(s). This results in poor oxygen diffusion from the air into the bloodstream. Widespread inflammation in the lung can contribute to the fibrosis. Interstitial lung disease includes as a class: silicosis; asbestosis; berylliosis; hypersensitivity pneumonitis; drug induced interstitial lung disease from, for example, antibiotics, chemotherapeutic drugs, and antiarrhythmic agents; systemic sclerosis; polymyositis; dermatomyositis; systemic lupus erythematosus; rheumatoid arthritis; atypical pneumonia; pneumocystis pneumonia (PCP); tuberculosis; sarcoidosis; idiopathic pulmonary fibrosis (IPF); hamman-rich syndrome IPF is a form of interstitial lung disease. There are several idiopathic forms of interstitial lung diseases, including and without limitation: usual interstitial pneumonia (UIP, which is now synonymous with idiopathic pulmonary fibrosis (IPF)); interstitial pneumonitis; nonspecific interstitial pneumonitis; bronchiolitis obliterans with organizing pneumonia (BOOP); respiratory bronchiolitis-associated interstitial lung disease; desquamative interstitial pneumonitis; lymphocytic interstitial pneumonitis; and acute interstitial pneumonitis.

MMP2 refers to human matrix metallopeptidase 2 (gelatinase A, 72 kDa gelatinase, 72 kDa type IV collagenase), GeneID: 4313, UniProtKB/Swiss-Prot: P08253 (FIG. 1, SEQ ID NO: 1), OMIM 120360 and GenBank Accession Nos. NM_001127891 (isoform b), NP_001121363 (isoform b), NM_004530 (isoform a), and NP_004521 (isoform a). These are exemplary sequences.

MMP7 refers to human matrix metallopeptidase 7 (matrilysin, uterine), GeneID: 4316, UniProtKB/Swiss-Prot: P09237 (FIG. 2, SEQ ID NO: 2), OMIM 178990 and GenBank Accession Nos. NM_002423 and NP_002414. These are exemplary sequences.

MMP8 refers to human matrix metallopeptidase 8 (neutrophil collagenase), GeneID: 4317, UniProtKB/Swiss-Prot: P22894 (FIG. 3, SEQ ID NO: 3, OMIM 120355 and GenBank Accession Nos. NM_002424 and NP_002415. These are exemplary sequences.

MMP9 refers to human matrix metallopeptidase 9 (gelatinase B, 92 kDa gelatinase, 92 kDa type IV collagenase), GeneID: 4318, UniProtKB/Swiss-Prot: P14780 (FIG. 4, SEQ ID NO: 4), OMIM 120361 and GenBank Accession Nos. NM_004994 and NP_004985. These are exemplary sequences.

An MMP activation peptide is a polypeptide or propeptide cleaved from a MMP upon activation. As indicated below, examples of MMP activation peptides include:

```
MMP2 activation peptide:
                            (SEQ ID NO: 1, bases 30-109)
APSPIIKFPGDVAPKTDKELAVQYLNTFYGCPKESCNLFVLKDTLKKMQ

KFFGLPQTGDLDQNTIETMRKPRCGNPDVAN;

MMP7 activation peptide:
                            (SEQ ID NO: 2, bases 18-94)
LPLPQEAGGMSELQWEQAQDYLKRFYLYDSETKNANSLEAKLKEMQKFF

GLPITGMLNSRVIEIMQKPRCGVPDVAE;

MMP8 activation peptide:
                            (SEQ ID NO: 3, bases 21-100)
FPVSSKEKNTKTVQDYLEKFYQLPSNQYQSTRKNGTNVIVEKLKEMQRF FGLNVTGKPNEETLDMMKKPRCGVPDSGGFM;
and MMP9 activation peptide:
                            (SEQ ID NO: 4, bases 20-93)
APRQRQSTLVLFPGDLRTNLTDRQLAEEYLYRYGYTRVAEMRGESKSLG

PALLLLQKQLSLPETGELDSATLKA.
```

Binding reagents specific to MMP2, 7, 8 and/or 9 activation peptides bind to and are specific to these polypeptides. Polyclonal or monoclonal antibodies specific to these MMP activation peptides are commercially available or may be readily raised to these polypeptides using standard methods for preparing polyclonal serum, monoclonal antibodies other binding reagents according to common methods known in the relevant arts.

An "immunoassay" is a qualitative and quantitative assay that detects and can quantify an amount of a particular compound, protein, polypeptide, molecule, etc. (collectively "ligand") in a biological sample, such as a urine, serum, blood, BAL, CSF (cerebrospinal fluid), saliva, or other samples taken from a patient, including refined preparations prepared from those biological samples, such as protein preparations, protein concentrates, fractions (e.g., prepared by size exclusion or affinity chromatography, precipitation, electrophoresis or any other method of separating a total protein preparation into two or more parts), filtration filtrates and residues, etc. In an immunoassay, binding or competition with binding of a ligand, such as one of MMP2, MMP7, MMP8, or MMP9 activation peptides (collectively "MMP activation peptides"), to a binding partner thereof, is detected and quantified. A large number of immunoassays useful in the methods described herein are known to those of ordinary skill in the fields of immunology, medical diagnostic, medicine, etc. An ELISA (Enzyme-Linked ImmunoSorbent Assay) is used in the examples, below to quantify MMP activation peptides. Other non-limiting examples of immunoassays include competitive and "sandwich" assays and include: enzyme-linked immunosorbent assay (ELISA), radioimmunoassay (RIA), agglutination test, competitive binding assay, bead-based assay, radioimmunoprecipitation assay, colloidal gold assays, lateral flow assay, fluorescence polarization assay, immunofluorescence assay, Western Blot, mass spectrometry, nuclear magnetic resonance, and chemiluminescence assay. Further the assays may be conducted in a variety of manners, including as a stand-alone assay or in an array.

The term "binding reagent" and like terms, refers to any compound, composition or molecule capable of specifically ("specifically" includes substantially specifically, that is, with limited cross-reactivity that does not interfere with the ability of the binding reagent to function in a given assay within acceptable tolerances) binding another compound or molecule (its "binding partner"), which, in the case of immune-recognition contains an epitope. In many instances, the binding reagents are antibodies, such as polyclonal or monoclonal antibodies. "Binding reagents" also include derivatives or analogs of antibodies, including without limitation: Fv fragments; single chain Fv (scFv) fragments; Fab' fragments; F(ab')2 fragments; humanized antibodies and antibody fragments; camelized antibodies and antibody fragments; and multivalent versions of the foregoing. Multivalent binding reagents also may be used, as appropriate, including without limitation: monospecific or bispecific antibodies, such as disulfide stabilized Fv fragments, scFv tandems ((scFv) fragments), diabodies, tribodies or tetrabodies, which typically are covalently linked or otherwise stabilized (i.e., leucine zipper or helix stabilized) scFv fragments, etc. "Binding reagents" also include aptamers, as are described in the art. Binding partners, such as, without limitation, biotin/avidin, receptor/substrate combinations and ligand/binding partner combinations also are considered to be within the class of "binding reagents." Antibodies and their respective antigens also are considered to be binding partners.

Binding reagents, such as antibodies, can be labeled by any useful method for detecting binding. For example and without limitation, reagent/antibody-labeling techniques are known for use in ELISA assays, including direct and indirect assays, sandwich-based assays, and competitive assays. Labels of antibodies include, without limitation, fluorophores, radioactive compounds, chemiluminescent compounds, chromatographic compounds, nanoparticles, colloids, beads, enzymes to cleave detectable substrates, and additional antibodies. In one embodiment, an antibody is labeled with an enzyme. Enzymes labeled to the antibody can be one or more of any known in the art. For example and without limitation, enzymes include horseradish peroxidase, glucose oxidase, beta galactosidase, beta lactamase, collagenase, and alkaline phosphatase. The antibody can be detected by using an enzyme-cleavable substrate and measuring the signal that arises from the substrate. The substrate can be a chromogenic or fluorogenic substrate. For example and without limitation, substrates include 3,3',5,5'-tetramethylbenzidene, diaminobenzidene, 2,2'-azino-bis-(3-ethylbenzothiazoline-6-sulfonic), fluorescein diphosphate, o-phenylenediamine, hydrogen peroxide, glucose, resorufin beta-D-galactopyranoside, fluorescein digalactoside, and p-nitrophenylphosphate.

In use, a binding reagent can be attached to a surface. In one embodiment, the binding reagent can be attached to a particle. For example and without limitation, particles include those comprising glass, polystyrene, polypropylene, polyethylene, dextran, nylon, amylases, natural and modified celluloses, polyacrylamides, agaroses, and magnetite. In another embodiment, the binding reagent can be attached to nanoparticles. In yet another embodiment, the binding reagent can be attached to a surface of a container. For example and without limitation, containers include microtiter plates, (multi) well plates, tubes, and petri dishes. In another embodiment, the binding reagent can be attached to a planar surface. For example and without limitation, surfaces include silicon chips, matrices of fibers, hydrogels, and membranes. Examples of fibers include, without limitation, nitrocellulose, cellulose, microcellulose, methylcellulose, carboxylmethylcellulose, starch, vinylalcohol, vinylpyrrolidone, polyvinylalcohol, poly(ethylene glycol), collagen, and gelatin.

An "array" refers either to a set of binding reagents immobilized onto one or more substrates so that each binding reagent is at a known location or a multi-chambered apparatus containing two or more discrete, identifiable reaction chambers, such as, without limitation a 96-well dish, in which reactions comprising identified constituents are performed. In an exemplary embodiment, a set of binding reagents is immobilized onto a surface in a spatially addressable manner so that each individual binding reagent is located at a different and identifiable location on the substrate. Substrates include, without limitation, multi-well plates and beads. In one embodiment, the beads contain a marker, such as a quantum dot or fluorescent tag, so that they are individually identifiable.

A method of quantifying activated MMP levels in urine may be performed in any feasible manner, as a single assay, in series or in parallel. Parallel screening may be performed in a multi-well dish, such as, without limitation a 96-well dish. Samples can be individually screened by binding reagent-MMP-binding in combination with any suitable binding detection method. Reactions can be performed in a suitable multi-well plate, for example and without limitation a 96-well plate or a 384-well plate. The choice of a suitable multi-well plate or reaction chamber is a matter of experimental design choice and depends on the nature of the assay, the number of assays to be run and the equipment available to perform the assay and detect binding of the reaction constituents. Fluorescence, color changes and/or luminescence can be detected using any one of a number of plate readers commercially available, such as, without limitation, TopCount NXT™ Microplate Scintillation and Luminescence Counters (PerkinElmer, Waltham, Massachusettes). Reactions can be wholly or partially automated using any one of a number of automated or semi-automated robotic fluid-handling devices available commercially.

In one embodiment, the methods described herein comprise determining levels of one or more of MMP2, MMP7, MMP8 or MMP9 activation peptides (propeptides), or combinations thereof in urine in a patient and identifying if one or more of MMP2, MMP7, MMP8 or MMP9 activation peptides (propeptides), or combinations thereof, in urine of the patient are elevated as compared to levels in a normal control (for example, values exceed a threshold level) as indicating the presence of interstitial lung disease, such as IPF, in the patient. In one embodiment, the levels are normalized to renal function in the patient, meaning they are adjusted based on a level of one or more constituents of urine that indicates kidney function. In the examples below, the concentration of the MMP activation peptides is normalized to creatinine levels in the urine samples from the patients, and values are expressed as a ratio of [MMP activation peptide]/[creatinine] (a ratio of the concentration of a MMP activation peptide to the concentration of creatinine, e.g., in ng/mL). Although preferable in many instances, the assays described herein are normalized to an indicator of kidney function. The methods are useful in identifying interstitial lung disease, monitoring interstitial lung disease progression, or determining effectiveness of treatment of an interstitial lung disease in a patient. In one embodiment, the patient is a human patient.

In one embodiment, values of MMP activation peptides are normalized, with threshold or cutoff values (values above which there is a statistically significant increased risk of pulmonary injury) for the MMP activation peptides being:

[MMP2 activation peptide]/[creatinine]≥0.6;
[MMP7 activation peptide]/[creatinine]≥1.255;
[MMP8 activation peptide]/[creatinine]≥0.195; and
[MMP9 activation peptide]/[creatinine]≥1.135.

Combinations of two or more of the above would increase the statistical significance of the results.

In one example, normalized levels of MMP activation peptides are used to define statistically significant thresholds or cutoffs indicative of lowered risk (or lack of risk) of interstitial lung disease in a patient. Thresholds for lowered risk of interstitial lung disease (e.g., IPF) include one or more of:

[MMP7 activation peptide]/[creatinine]<1.255;
[MMP7 activation peptide]/[creatinine]≥1.255, [MMP9 activation peptide]/[creatinine]<1.135 and [MMP8 activation peptide]/[creatinine]<0.195; or
[MMP7 activation peptide]/[creatinine]≥1.255, [MMP9 activation peptide]/[creatinine]≥1.135 and [MMP2 activation peptide]/[creatinine]<0.6.

Exemplary thresholds for interstitial lung disease (e.g., IPF) in the patient include one or more of:

[MMP7 activation peptide]/[creatinine]≥1.255, [MMP9 activation peptide]/[creatinine]<1.135 and [MMP8 activation peptide]/[creatinine]≥0.195; or
[MMP7 activation peptide]/[creatinine]≥1.255, [MMP9 activation peptide]/[creatinine]≥1.135 and [MMP2 activation peptide]/[creatinine]≥0.6.

In another embodiment, values of MMP activation peptides are not normalized, with threshold or cutoff values (values above which there is a statistically significant increased likelihood of interstitial lung disease (e.g., IPF)) for the MMP activation peptides in ng/mL being:

MMP2>0.780 ng/mL;
MMP7>1.225 ng/mL;
MMP8>0.440 ng/mL; and
MMP9>1.240 ng/mL.

Combinations of two or more of the above would increase the statistical significance of the results.

It should be noted that the values and ratios provided are merely exemplary and mathematically can be expressed in a large variety or ways. For example 10 ng/mL can be expressed as 10000 pg/mL or 0.01 µg/mL. Likewise the ratio of [MMP activation peptide]/[creatinine] can be expresses as its inverse; that is, [creatinine]/[MMP activation peptide]. Thus the cutoff of [MMP9 activation peptide]/[creatinine] <1.135 would be [creatinine]/[MMP9 activation peptide]>1/1.135 (or 0.881).

The degree to which the levels of the one or more MMP activation peptides are elevated in order to identify interstitial lung disease (e.g., IPF) in a patient are determined experimentally, as is demonstrated herein, and are statistically significant. By "statistically significant" it is meant that, irrespective of the mathematical/statistical methodology used, the levels or cutoffs used to distinguish increased risk versus less risk of interstitial lung disease in a patient yield clinically acceptable results are capable of distinguishing risk versus lack of risk in more than 50%, 60%, 70%, 75%, 80%, 90%, 95%, 97% or 90% of patients. While clinical assays rarely are 100% accurate, 90% or greater accuracy in diagnosis of risk is preferred. Thus, the exemplary cutoffs presented in FIG. 3B, expressed in terms of cutoffs presented as the normalized ratio of [MMP activation protein in ng/mL]/[creatinine in mg/mL] is statistically significant as the accuracy (e.g., the specificity and selectivity) of the described cutoffs in distinguishing individuals having interstitial lung disease, from individuals at lower risk is above clinically-acceptable levels. A patient fitting into the high risk profile as indicated by levels of the respective MMP activation peptides as shown in FIG. 3B, is preferably treated medically for IPF or pulmonary injury.

In one embodiment, the step of detection of levels of one or more of MMP2, MMP7, MMP8 or MMP9 is performed and the values are either automatically or manually entered into a computer process (a software and/or hardware-implemented computer task implemented in/on/by a computing device, e.g. a personal computer, laptop, PDA, smart phone). The process comprises computer code, functions, algorithms, etc., that compares data to threshold data values input and/or stored within or configured into the process and outputs the data and optionally a outputs values/data/indicia indicating risk of interstitial lung disease in a useful form, such as a printout or visual display and/or stores the data and/or results of analysis of the data in a computer-readable form, such as on a optical disc (e.g., CD or DVD), hard drive, ROM, RAM, memory card, networked drive, tape drive, etc. Design and implementation of useful processes is well within the abilities of those of ordinary skill in the art of computer software/process design.

EXAMPLE

Methods

Reagents

All antibodies were commercially available. A rabbit polyclonal to the MMP8 propeptide domain was obtained from Abcam (Cambridge, Mass.). A mouse monoclonal antibody to the N-terminus of MMP2 (APSPIIKFPGDVAPKTDK, SEQ ID NO: 1, bases 30-47) was obtained from Thermo Scientific (Fremont, Calif.). A rabbit monoclonal antibody to the propeptide domain of MMP9 was obtained from Novus Biologicals (Littleton, Colo.). MMP7 propeptide antibody was obtained from R&D Systems (Minneapolis, Minn.). Polypeptides corresponding to the N-terminus of each MMP propeptide (activation peptide) were synthetically made by Genscript (MMP2, 7, 9) (Piscataway, N.J.) or Abcam (MMP8) (Cambridge, Mass.). All antibodies cross react with human and mouse.

Patient Urine Collection and Processing

Sixty eight samples were analyzed in this study, including samples from patients diagnosed with IPF (n=42) and controls (n=30). IPF groups and controls were comparable with respect to age both in terms of the mean (64, 59) and the range (40-81, 50-82). Control urine was purchased from Bioreclamation Inc. (Hicksville, N.Y.). Samples were collected in sterile containers and immediately frozen at −20° C. The samples were thawed, and creatinine concentrations were determined according to manufacturer's instructions (R&D Systems Minneapolis, Minn.). Urine containing blood or leukocytes as determined by Multistix 9 Urinalysis Strips (Bayer) was excluded. Protein concentration of urine was determined by the Bradford method using bovine serum albumin as the standard. Urine samples were centrifuged using Microcon Centrifugal Filter Devices Ultracel YM-10 (Millipore Corporation, Billerica, Mass.). Retentate was discarded and flow through (<10 kd) was used for analysis.

Enzyme-Linked Immunosorbent Assays (ELISAs)

Costar 96-well RIA/EIA plates (Costar, Cambridge, Mass.) were incubated overnight at 4° C. with sample to be tested, in a total volume of 50 µl. Wells containing known concentrations of activation peptide were simultaneously analyzed. Coated plates were washed and blocked with PBS 1% BSA, 5% sucrose, 0.05% $NaN_3$ (blocking buffer) for 2 hours at 37° C. Plates were washed with blocking buffer then incubated with 100 µl of MMP antisera specific to the activation peptide of interest diluted in blocking buffer for 1 h at 37° C. The plates were washed and incubated for 1 hr using 100 µl (1/2000 dilution) of Horseradish peroxidase coupled antibody (either anti-mouse IgG or anti-rabbit IgG). After washing with blocking buffer and PBS, the substrate o-Phenylenediamine Dihydrochloride (Sigma) was added. Horseradish peroxidase activity was read at 450 nm using a THERMOmax microplate reader (Molecular Devices, Menlo Park, Calif.).

Mouse Treatment and Urine Collection 8-10 wk. old male C57BL/6 mice (Taconic, Germantown, N.Y.) were treated with a single 0.1-mg dose of crocidolite asbestos, 0.05 units of Bleomycin, or 0.9% Saline by intratracheal instillation as previously described (12). Each mouse was individually placed in a plastic beaker and allowed to urinate. Immediately after urination, the mouse was removed and the voided urine was aspirated and transferred into a sterile micro-centrifuge tube. Samples were taken at day 0 prior to treatment and everyday following treatment. Urine volumes raged from 10 µl-300 µl per mouse. Samples were processed and stored as described for human samples.

Statistical Methods

Data are presented as mean±standard deviation. The Wilcoxon rank-sum test was used to identify which of the four markers univariately distinguish IPF samples from controls. Data were analyzed using the R language for statistical computing (http://www.r-project.org/) (13). Classification and regression trees (CART) methodology was used to identify potential combinations of markers that could be used to distinguish IPF from controls. CART was performed using the rpart package for recursive partitioning. Classification performance was assessed using the ROCR package (http://rocr.bioinf.mpi-sb.mpg.de/).

Results

ELISA Validation

MMP2, 7, 8, and 9 map to different chromosome regions of the human genome but are individually conserved across species with 79% (MMP2), 75% (MMP7), 80% (MMP8) and 96% (MMP9) homology to the respective mouse MMP. The protein structure of human MMPs includes a pro domain that consists of 80 to 90 amino acids (TABLE 1). The pro domain or activation peptide is cleaved from the latent protein upon activation and is detectable in the urine of mice and humans.

To quantitate the release of MMP activation peptides into the urine, antibodies against the pro domain of each MMP were used.

TABLE 1

Human MMP Characteristics

| Enzyme | Family name | Mol. Wt. (Pro peptide) |
|---|---|---|
| MMP2 | Gelatinase | 8934.42 |
| MMP7 | Matrilysin | 8822.25 |
| MMP8 | Collagenase | 9210.61 |
| MMP9 | Gelatinase | 8339.62 |

The determined sensitivity of the assay is <1 ng/ml. Standard curves were generated using serial dilutions of synthetic peptide corresponding to the pro peptide domain of MMP2, MMP7, MMP8, and MMP9 in phosphate buffered saline (PBS) starting with 10 ng/ml for MMP2, 7, and 8 activation peptides, and 1 ng/ml for MMP9 activation peptide (data not shown). Sensitivity of these assays was defined as the lowest MMP activation peptide concentration that could be differentiated from zero (assay blank/PBS) by Student's t-test.

The reproducibility of the assay is determined by assessing the precision profile by using urine samples that were known to be positive for each MMP activation peptide assayed at a concentration above the midpoint of the detection rage. Inter- and intra-assay CVs ranged from 5.7% to 7.9% (n=10) and from 6.3% to 9.9% (n=2 in 10 different plates), respectively (FIG. 5A, B).

To determine the dilution linearity we used a known positive urine sample containing between 2 and 3.5 ng/ml corresponding to medium concentrations of MMP activation peptide and diluted it 1:5, 1:10, and 1:20, the sample gave results close to linearity (r=0.95-0.99) (FIG. 5C).

Figure 6:
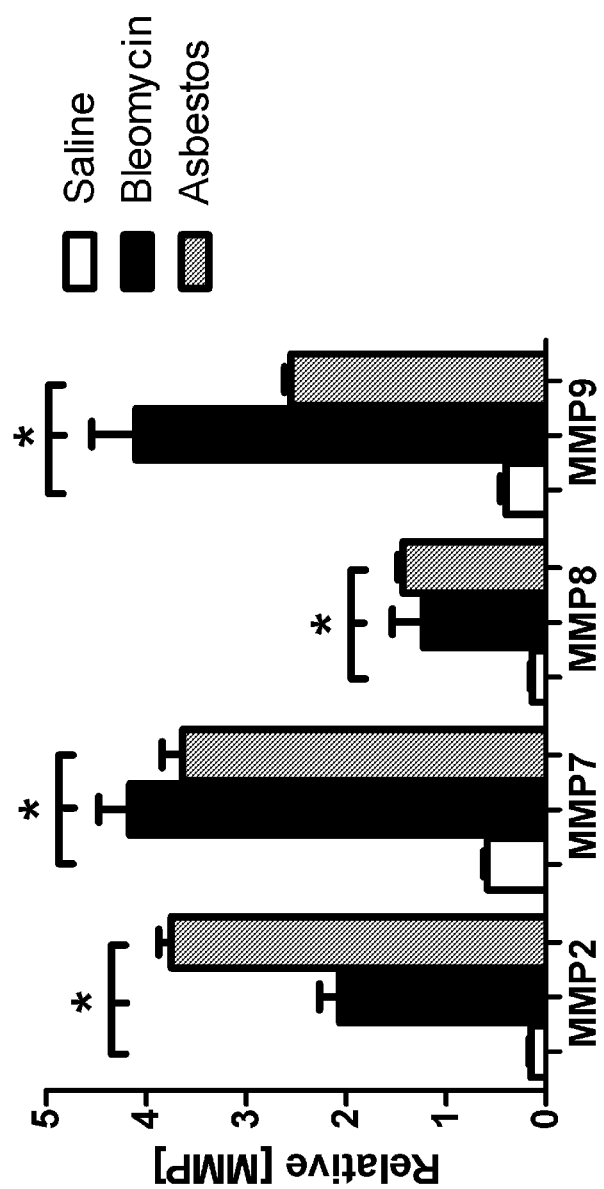
FIG. 6. MMP Activation Peptides are Detectable and Elevated in the Urine of Mice with Pulmonary Fibrosis. Activation peptides of MMP2, MMP7, MMP8 and MMP9 are detectable in the urine of mice via ELISA. All four are significantly increased in the urine of mice treated with bleomycin (black bars) or asbestos (gray bars) compared to the urine of control mice treated only with saline (white bars) ($*p<0.05$).

Activation Peptides from MMP2, MMP7, MMP8, and MMP9 are Increased in the Urine of Mice Following Pulmonary Injury To determine if the activation peptides of MMP2, MMP7, MMP8 and MMP9 are detectable in the urine of mice following pulmonary injury we used the same ELISA used for the human samples. For this study we collected urines from C57BL/6 mice prior to and following asbestos and bleomycin induced pulmonary injury. The mice were treated intratracheally with either 0.1-mg of asbestos, 0.05 units of bleomycin, or saline only. Urines were collected at day 0 prior to treatment and then everyday post treatment. Our results show that all of the markers assessed are significantly increased in the urine of mice with pulmonary injury compared to the urine of mice treated only with saline ∆t day 14, when it has been shown that these mouse models are exhibiting detectable fibrosis, it is clear that the activation peptide levels are significantly increased in the urines of the injured mice compared to controls (FIG. 6).

Patient Characteristics

Demographic data, urine MMP activation peptide concentrations, urine creatinine levels and pulmonary function test results are summarized in Table 2. IPF patients were diagnosed via lung biopsy or radiographic evidence and normal controls (NC) were healthy age range matched with a similar gender distribution. Pulmonary function tests reveal that there is no significant correlation between urine MMP activation peptide concentrations and forced vital capacity (FVC %) or carbon monoxide diffusing capacity ($DL_{CO}$ %).

TABLE 2

Patient Characteristics and MMP Activation Peptide Levels

Figure 7A:
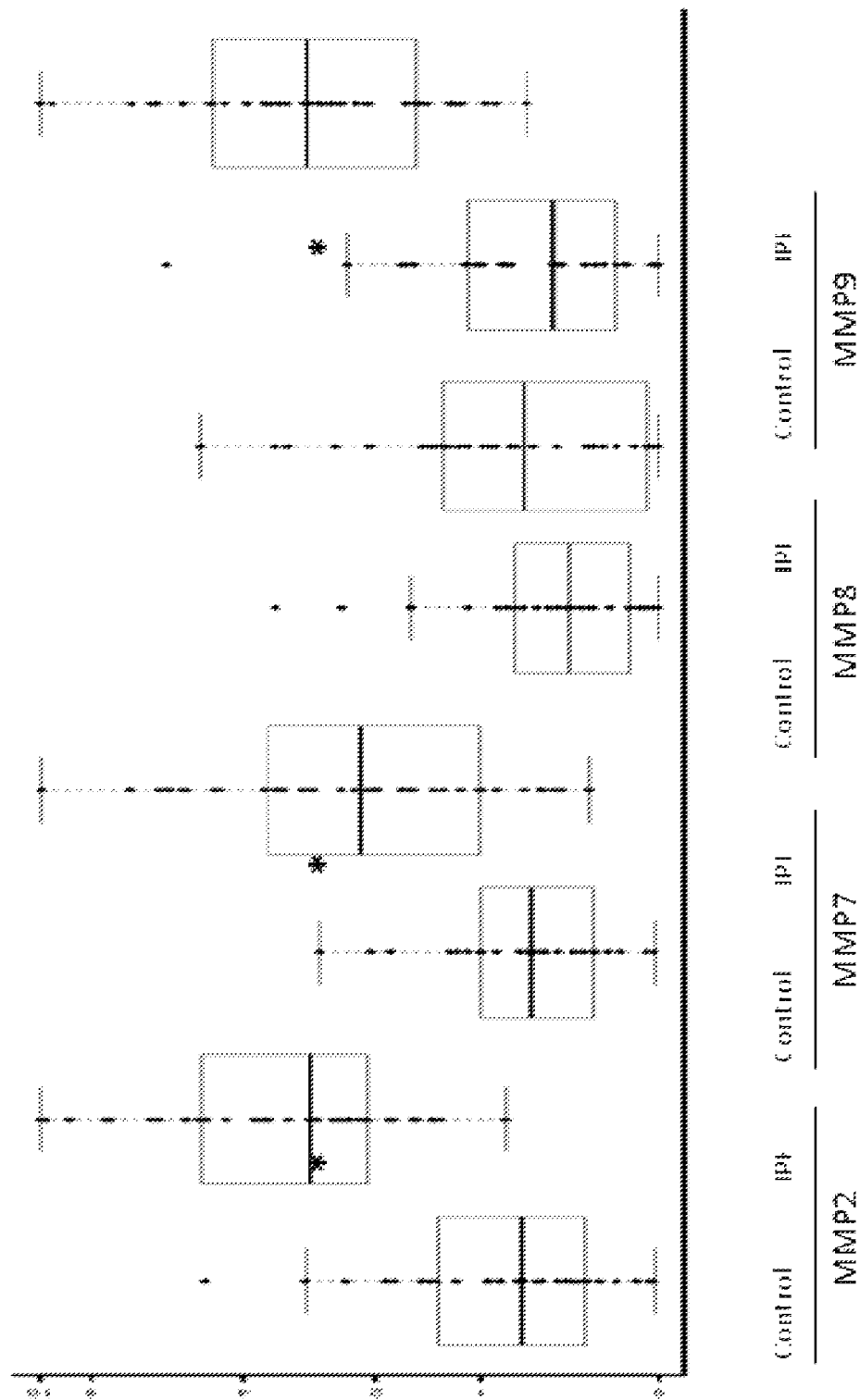
FIGS. 7A-7C. Urine MMP Activation Peptides Distinguish IPF Patients From Controls.
Figure 7B:
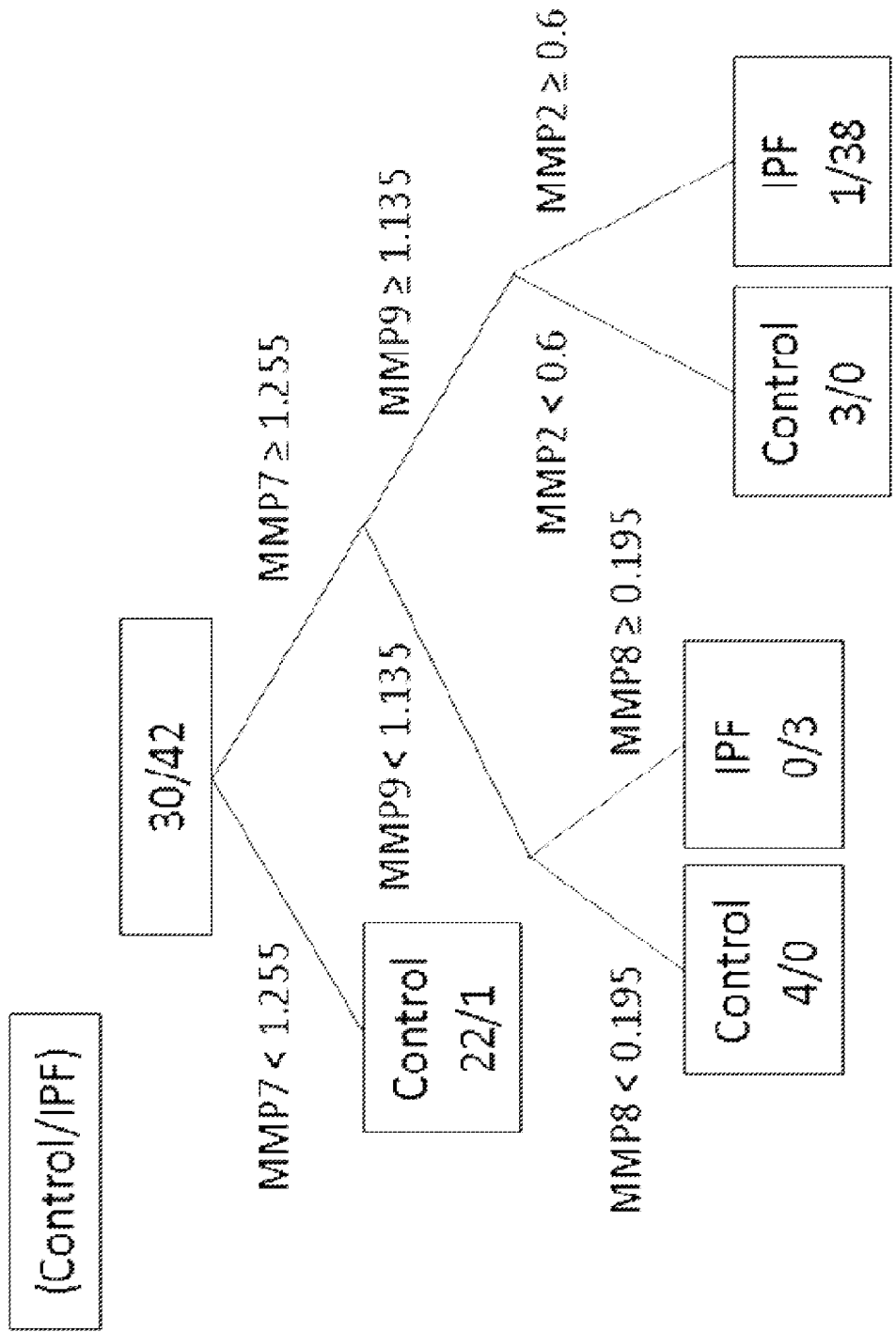
Figure 7C:
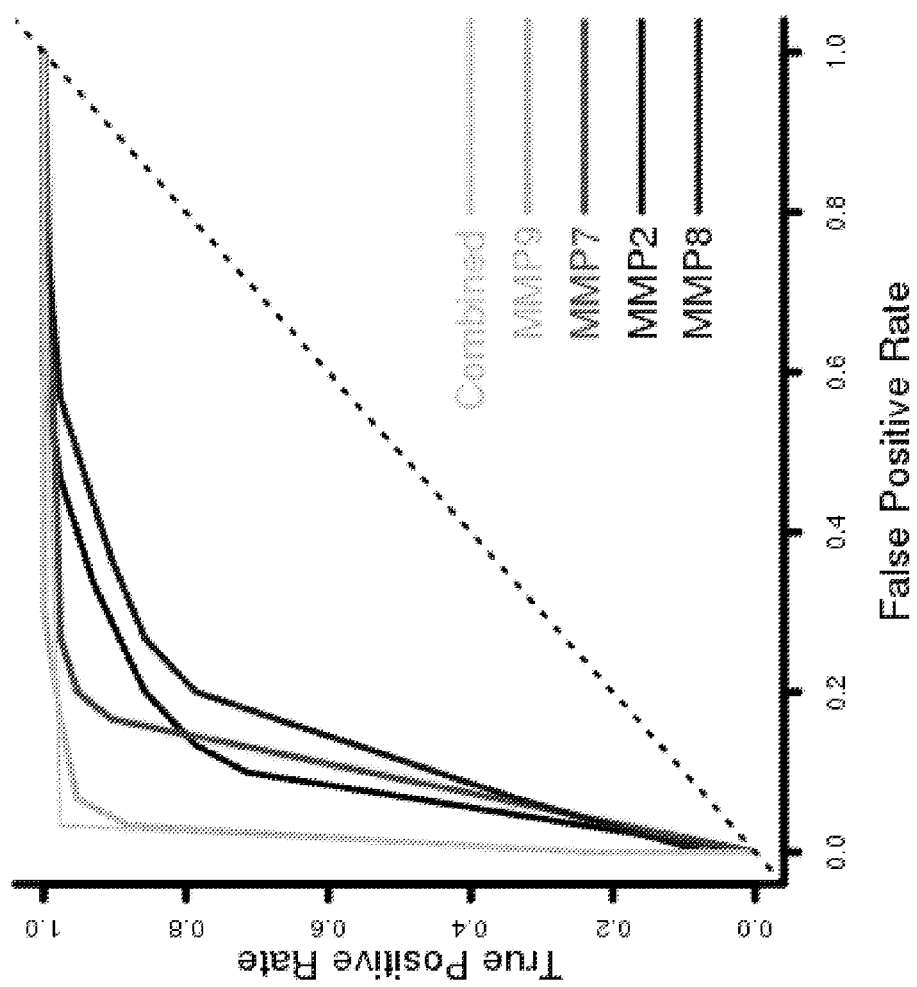

| Variable | IPF | NC |
|---|---|---|
| Age | 65.7 ± 11.4 | 59.5 ± 8.8 |
| Sex, male/female | 38/5 ?? | 24/6 |
| Creatinine | 183.3 ± 74.2 | 132 ± 75.5 |
| PFT Fvc % | 66.74 ± 13.94 | — |
| PFT DlCo % | 50.49 ± 17.23 | — |
| [MMP2 activation peptide]* | 2.6 ± 2.0 | .76 ± .61 |
| [MMP7 activation peptide]* | 3.6 ± 2.6 | .97 ± 1.0 |
| [MMP8 activation peptide]* | .88 ± 1.0 | 0.6 ± .74 |
| [MMP9 activation peptide]* | 3.3 ± 2.4 | .87 ± 1.1 | is almost guaranteed to be an IPF patient. Relative urine concentrations of MMP8 activation peptide are not independently important. Receiver operating characteristic curves (ROCS) agree that a combination of the four markers, most significantly the combination of the activation peptides of MMP2, MMP7, and MMP9 correctly classify IPF patients from controls (FIG. 7C).

Figure 8:
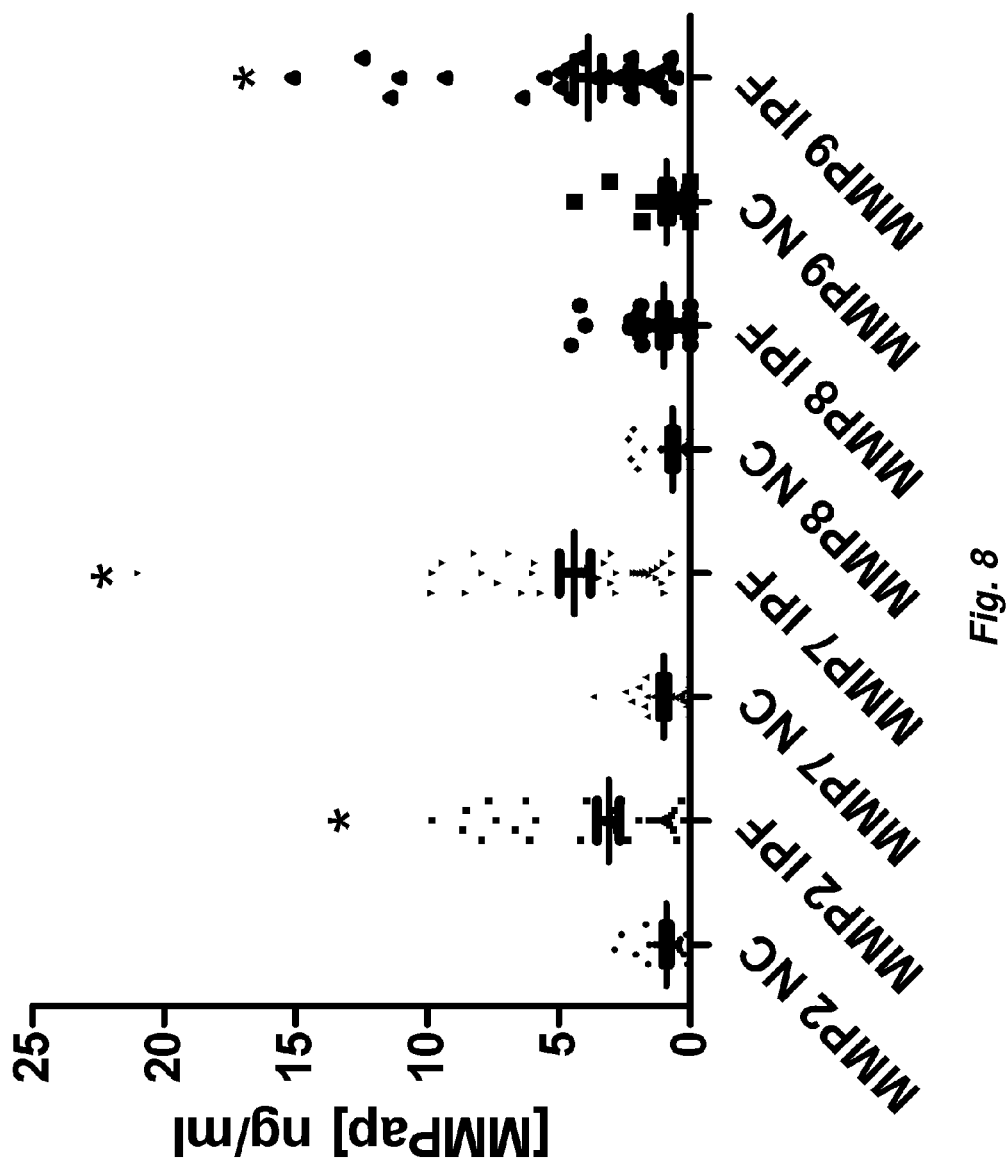
FIG. 8 is a graph of the data provided in Table 3, illustrating MMP activation peptide levels in IPF patients versus healthy age-matched controls.

Table 3 (see also FIG. 8) provides raw data for the MMP activation peptide levels described above. Of note, even without normalization, quantification of levels of MMP activation peptide levels can be used clinically to classify patients having interstitial lung disease (e.g., IPF) and lower risk of interstitial lung disease (e.g., IPF). The following cutoffs are capable of classifying patients having higher and lower risk of pulmonary injury.

TABLE 3

| | MMP2 NC | MMP2 IPF | MMP7 NC | MMP7 IPF | MMP8 NC | MMP8 IPF | MMP9 NC | MMP9 IPF |
|---|---|---|---|---|---|---|---|---|
| Number of values | 30 | 42 | 30 | 42 | 30 | 42 | 30 | 42 |
| Minimum | 0.04 | 0.25 | 0.06 | 0.69 | 0 | 0 | 0 | 0.55 |
| 25% Percentile | 0.415 | 0.955 | 0.325 | 1.668 | 0.215 | 0.07 | 0.1925 | 1.903 |
| Median | 0.715 | 1.78 | 0.89 | 3.155 | 0.31 | 0.58 | 0.79 | 2.62 |
| 75% Percentile | 1.36 | 4.598 | 1.633 | 6.108 | 1.053 | 1.685 | 1.153 | 4.57 |
| Maximum | 2.89 | 9.85 | 3.68 | 21 | 2.35 | 4.53 | 4.4 | 15.13 |
| Mean | 0.9053 | 3.067 | 1.015 | 4.329 | 0.6783 | 0.9917 | 0.899 | 3.82 |
| Std. Deviation | 0.7278 | 2.758 | 0.8476 | 3.8 | 0.7279 | 1.159 | 0.9453 | 3.353 |
| Std. Error | 0.1329 | 0.4256 | 0.1548 | 0.5863 | 0.1329 | 0.1788 | 0.1726 | 0.5173 |
| Lower 95% CI of mean | 0.6336 | 2.207 | 0.6981 | 3.145 | 0.4065 | 0.6305 | 0.546 | 2.775 |
| Upper 95% CI of mean | 1.177 | 3.926 | 1.331 | 5.513 | 0.9501 | 1.353 | 1.252 | 4.865 |
| Sum | 27.16 | 128.8 | 30.44 | 181.8 | 20.35 | 41.65 | 26.97 | 160.4 |

MMP Activation Peptide Concentrations are Different Between IPF Patients and Controls To determine whether urine MMP2, MMP7, MMP8, and MMP9 activation peptide concentrations were higher in IPF patients compared to controls, we measured their levels in 42 patients with IPF and 30 healthy age range matched controls via ELISA. The resulting concentrations are relative to each patient's urine creatinine level. Univariately, the relative urine concentrations of the activation peptides of MMP2 ($p<0.001$), MMP7 ($p<0.001$), and MMP9 ($p<0.001$) are significantly higher in IPF patients compared to controls (FIG. 7A). MMP8 activation peptide levels were slightly increased in IPF urines but not significantly.

We used recursive partitioning (CART) to determine whether these 4 markers in the urine comprise a combinatorial classifier to correctly classify IPF patients from controls. The results suggest that these markers in the urine can be used to distinguish IPF from control with high sensitivity (97.6% CI (0.874, 0.999)) and specificity (96.7% CI (0.828, 0.999)). Low relative concentrations of MMP7 activation peptide alone ($\leq 1.255$) correctly exclude 41 of 42 IPF patients but incorrectly classify 1 normal sample as IPF and 1 IPF sample as control whereas the combination of high relative urine concentrations of MMP7 ($\geq 1.255$), MMP2 ($\geq 0.985$), and MMP9 ($\geq 1.135$) exclude all controls but 1. Therefore, if MMP7 is low, then a randomly selected case is almost guaranteed not to be an IPF patient (FIG. 7B). Further, if MMPs 7, 9, and 2 are all simultaneously high, a randomly selected case Table 4 provides examples of clinically relevant cutoff (threshold values, above which a patient exhibits increased risk of having or developing IPF) values along with their respective sensitivity/specificity values. These data were obtained via ROC curve analysis (similar to FIG. 7C). Statistical analysis using CART analysis (as in FIG. 7B) is expected to yield cutoffs with higher sensitivity and specificity.

TABLE 4

| | Cutoff (ng/ml) | Sensitivity % | 95% CI | Specificity % | 95% CI | Likelihood ratio |
|---|---|---|---|---|---|---|
| MMP2 | >0.780 | 85.71 | 71.46% to 94.57% | 63.33 | 43.86% to 80.07% | 2.34 |
| MMP7 | >1.225 | 88.1 | 74.37% to 96.02% | 70 | 50.60% to 85.27% | 2.94 |
| MMP8 | >0.440 | 59.52 | 43.28% to 74.37% | 60 | 40.60% to 77.34% | 1.49 |
| MMP9 | >1.240 | 85.71 | 71.46% to 94.57% | 83.33 | 65.28% to 94.36% | 5.14 |

Having described this invention above, it will be understood to those of ordinary skill in the art that the same can be performed within a wide and equivalent range of conditions, formulations and other parameters without affecting the scope of the invention or any embodiment thereof.

We claim:

1. A method of identifying interstitial lung disease, monitoring interstitial lung disease progression, or determining effectiveness of treatment of an interstitial lung disease in a patient, comprising determining a level of one or more of MMP2 activation peptide, MMP7 activation peptide, MMP8 activation peptide and MMP9 activation peptide in urine of the patient, and identifying whether the patient has interstitial lung disease by determining if levels of one or more of MMP2 activation peptide, MMP7 activation peptide, MMP8 activation peptide and MMP9 activation peptide in urine of the patient exceed a threshold level indicative of interstitial lung disease.

2. The method of claim 1, wherein the interstitial lung disease includes fibrosis.

3. The method of claim 1, wherein the interstitial lung disease is idiopathic pulmonary fibrosis (IPF).

4. The method of claim 1, comprising determining a level of one or more of MMP2 activation peptide, MMP7 activation peptide and MMP9 activation peptide in urine of the patient and identifying whether the patient has interstitial lung disease by determining if levels of one or more of MMP2 activation peptide, MMP7 activation peptide and MMP9 activation peptide in urine of the patient exceed a threshold level indicative of interstitial lung disease.

5. The method of claim 3, comprising determining levels of MMP2 activation peptide, MMP7 activation peptide and MMP9 activation peptide in urine of the patient and identifying whether the patient has interstitial lung disease by determining if levels of MMP2 activation peptide, MMP7 activation peptide and MMP9 activation peptide in urine of the patient exceed a threshold level indicative of interstitial lung disease.

6. The method of claim 1, further comprising normalizing the determined levels of one or more of MMP2 activation peptide, MMP7 activation peptide, MMP8 activation peptide and MMP9 activation peptide in urine of the patient to an indicator of kidney function, and identifying whether the patient has interstitial lung disease by determining if the normalized levels of one or more of MMP2, MMP7, MMP8 and MMP9 in urine of the patient exceed a threshold level indicative of interstitial lung disease.

7. The method of claim 6, wherein the indicator of kidney function is creatinine concentration in the patient's urine.

8. The method of claim 7, wherein the normalized levels of one or more of MMP2 activation peptide, MMP7 activation peptide, MMP8 activation peptide and MMP9 activation peptide are expressed as [MMP activation peptide]/[creatinine] in the patient's urine.

9. The method of claim 6, in which one of:
   a. [MMP7 activation peptide]/[creatinine]<1.255;
   b. [MMP7 activation peptide]/[creatinine]≥1.255, [MMP9 activation peptide]/[creatinine]<1.135 and [MMP8 activation peptide]/[creatinine]<0.195; or
   c. [MMP7 activation peptide]/[creatinine]≥1.255, [MMP9 activation peptide]/[creatinine]≥1.135 and [MMP2 activation peptide]/[creatinine]<0.6 in urine of the patient indicates lowered risk of having an interstitial lung disease in the patient.

10. The method of claim 6, in which one of:
   a. [MMP7 activation peptide]/[creatinine]≥1.255, [MMP9 activation peptide]/[creatinine]<1.135 and [MMP8 activation peptide]/[creatinine]≥0.195; or
   b. [MMP7 activation peptide]/[creatinine]≥1.255, [MMP9 activation peptide]/[creatinine]≥1.135 and [MMP2 activation peptide]/[creatinine]≥0.6 indicates interstitial lung disease in the patient.

11. The method of claim 1, in which the threshold level is statistically significant.

12. The method of claim 1, wherein the levels of one or more of MMP2 activation peptide, MMP7 activation peptide, MMP8 activation peptide and MMP9 activation peptide in urine of the patient are determined by immunoassay.

13. The method of claim 1, wherein the levels of one or more of MMP2 activation peptide, MMP7 activation peptide, MMP8 activation peptide and MMP9 activation peptide in urine of the patient are determined by ELISA.

14. The method of claim 1, comprising determining a level of MMP2 activation peptide using a binding reagent specific to a polypeptide having the sequence:

```
                          (SEQ ID NO: 1, bases 30-109)
APSPIIKFPGDVAPKTDKELAVQYLNTFYGCPKESCNLFVLKDTLKKMQ

KFFGLPQTGDLDQNTIETMRKPRCGNPDVAN.
```

15. The method of claim 1, comprising determining a level of MMP7 activation peptide using a binding reagent specific to a polypeptide having the sequence:

```
                          (SEQ ID NO: 2, bases 18-94)
LPLPQEAGGMSELQWEQAQDYLKRFYLYDSETKNANSLEAKLKEMQKFF

GLPITGMLNSRVIEIMQKPRCGVPDVAE.
```

16. The method of claim 1, comprising determining a level of MMP8 activation peptide using a binding reagent specific to a polypeptide having the sequence:

```
                          (SEQ ID NO: 3, bases 21-100)
FPVSSKEKNTKTVQDYLEKFYQLPSNQYQSTRKNGTNVIVEKLKEMQRF

FGLNVTGKPNEETLDMMKKPRCGVPDSGGFM.
```

17. The method of claim 1, comprising determining a level of MMP9 activation peptide using a binding reagent specific to a polypeptide having the sequence:

```
                          (SEQ ID NO: 4, bases 20-93)
APRQRQSTLVLFPGDLRTNLTDRQLAEEYLYRYGYTRVAEMRGESKSLG

PALLLLQKQLSLPETGELDSATLKA.
```

18. The method of claim 1, in which the patient is a human patient.

19. A kit comprising binding reagents specific to MMP9 activation peptide, MMP7 activation peptide, and one or both of MMP2 activation peptide and MMP8 activation peptide and one or more detection reagents for detecting binding of the binding reagents to MMP9 activation peptide, MMP7 activation peptide, and one or both of MMP2 activation peptide and MMP8 activation peptide.

20. The kit of claim 19, in which the binding reagents are antibodies.

21. The kit of claim 19, in which the detection reagents comprise antibodies for binding to the antibodies specific to MMP9 activation peptide, MMP7 activation peptide, and one or both of MMP2 activation peptide and MMP8 activation peptide and a label, optionally attached to the detection reagent.

22. The kit of claim 21, in which the label comprises one of an enzyme, a fluorophore, a quantum dot, a colloid, a radionuclide, a radioisotope, and a chromophore.

\* \* \* \* \*

UNITED STATES PATENT AND TRADEMARK OFFICE
CERTIFICATE OF CORRECTION

PATENT NO. : 8,568,996 B2  Page 1 of 1
APPLICATION NO. : 13/121142
DATED : October 29, 2013
INVENTOR(S) : Enghild et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 369 days.

Signed and Sealed this

Fifteenth Day of September, 2015

Michelle K. Lee
*Director of the United States Patent and Trademark Office*

SEQUENCE LISTING

<160> NUMBER OF SEQ ID NOS: 4

<210> SEQ ID NO 1
<211> LENGTH: 660
<212> TYPE: PRT
<213> ORGANISM: Homo sapiens

<400> SEQUENCE: 1

```
Met Glu Ala Leu Met Ala Arg Gly Ala Leu Thr Gly Pro Leu Arg Ala
 1               5                  10                  15

Leu Cys Leu Leu Gly Cys Leu Leu Ser His Ala Ala Ala Pro Ser
                20                  25                  30

Pro Ile Ile Lys Phe Pro Gly Asp Val Ala Pro Lys Thr Asp Lys Glu
            35                  40                  45

Leu Ala Val Gln Tyr Leu Asn Thr Phe Tyr Gly Cys Pro Lys Glu Ser
    50                  55                  60

Cys Asn Leu Phe Val Leu Lys Asp Thr Leu Lys Lys Met Gln Lys Phe
65                  70                  75                  80

Phe Gly Leu Pro Gln Thr Gly Asp Leu Asp Gln Asn Thr Ile Glu Thr
                85                  90                  95

Met Arg Lys Pro Arg Cys Gly Asn Pro Asp Val Ala Asn Tyr Asn Phe
            100                 105                 110

Phe Pro Arg Lys Pro Lys Trp Asp Lys Asn Gln Ile Thr Tyr Arg Ile
        115                 120                 125

Ile Gly Tyr Thr Pro Asp Leu Asp Pro Glu Thr Val Asp Asp Ala Phe
130                 135                 140

Ala Arg Ala Phe Gln Val Trp Ser Asp Val Thr Pro Leu Arg Phe Ser
145                 150                 155                 160

Arg Ile His Asp Gly Glu Ala Asp Ile Met Ile Asn Phe Gly Arg Trp
                165                 170                 175

Glu His Gly Asp Gly Tyr Pro Phe Asp Gly Lys Asp Gly Leu Leu Ala
            180                 185                 190

His Ala Phe Ala Pro Gly Thr Gly Val Gly Gly Asp Ser His Phe Asp
        195                 200                 205

Asp Asp Glu Leu Trp Thr Leu Gly Glu Gly Gln Val Val Arg Val Lys
    210                 215                 220

Tyr Gly Asn Ala Asp Gly Glu Tyr Cys Lys Phe Pro Phe Leu Phe Asn
225                 230                 235                 240

Gly Lys Glu Tyr Asn Ser Cys Thr Asp Thr Gly Arg Ser Asp Gly Phe
                245                 250                 255

Leu Trp Cys Ser Thr Thr Tyr Asn Phe Glu Lys Asp Gly Lys Tyr Gly
            260                 265                 270

Phe Cys Pro His Glu Ala Leu Phe Thr Met Gly Gly Asn Ala Glu Gly
        275                 280                 285

Gln Pro Cys Lys Phe Pro Phe Arg Phe Gln Gly Thr Ser Tyr Asp Ser
    290                 295                 300

Cys Thr Thr Glu Gly Arg Thr Asp Gly Tyr Arg Trp Cys Gly Thr Thr
305                 310                 315                 320

Glu Asp Tyr Asp Arg Asp Lys Lys Tyr Gly Phe Cys Pro Glu Thr Ala
                325                 330                 335

Met Ser Thr Val Gly Gly Asn Ser Glu Gly Ala Pro Cys Val Phe Pro
            340                 345                 350

Phe Thr Phe Leu Gly Asn Lys Tyr Glu Ser Cys Thr Ser Ala Gly Arg
        355                 360                 365
```

```
Ser Asp Gly Lys Met Trp Cys Ala Thr Thr Ala Asn Tyr Asp Asp Asp
370                 375                 380

Arg Lys Trp Gly Phe Cys Pro Asp Gln Gly Tyr Ser Leu Phe Leu Val
385                 390                 395                 400

Ala Ala His Glu Phe Gly His Ala Met Gly Leu Glu His Ser Gln Asp
            405                 410                 415

Pro Gly Ala Leu Met Ala Pro Ile Tyr Thr Tyr Thr Lys Asn Phe Arg
            420                 425                 430

Leu Ser Gln Asp Asp Ile Lys Gly Ile Gln Glu Leu Tyr Gly Ala Ser
            435                 440                 445

Pro Asp Ile Asp Leu Gly Thr Gly Pro Thr Pro Thr Leu Gly Pro Val
450                 455                 460

Thr Pro Glu Ile Cys Lys Gln Asp Ile Val Phe Asp Gly Ile Ala Gln
465                 470                 475                 480

Ile Arg Gly Glu Ile Phe Phe Phe Lys Asp Arg Phe Ile Trp Arg Thr
            485                 490                 495

Val Thr Pro Arg Asp Lys Pro Met Gly Pro Leu Leu Val Ala Thr Phe
            500                 505                 510

Trp Pro Glu Leu Pro Glu Lys Ile Asp Ala Val Tyr Glu Ala Pro Gln
515                 520                 525

Glu Glu Lys Ala Val Phe Phe Ala Gly Asn Glu Tyr Trp Ile Tyr Ser
530                 535                 540

Ala Ser Thr Leu Glu Arg Gly Tyr Pro Lys Pro Leu Thr Ser Leu Gly
545                 550                 555                 560

Leu Pro Pro Asp Val Gln Arg Val Asp Ala Ala Phe Asn Trp Ser Lys
            565                 570                 575

Asn Lys Lys Thr Tyr Ile Phe Ala Gly Asp Lys Phe Trp Arg Tyr Asn
            580                 585                 590

Glu Val Lys Lys Lys Met Asp Pro Gly Phe Pro Lys Leu Ile Ala Asp
            595                 600                 605

Ala Trp Asn Ala Ile Pro Asp Asn Leu Asp Ala Val Val Asp Leu Gln
610                 615                 620

Gly Gly Gly His Ser Tyr Phe Phe Lys Gly Ala Tyr Tyr Leu Lys Leu
625                 630                 635                 640

Glu Asn Gln Ser Leu Lys Ser Val Lys Phe Gly Ser Ile Lys Ser Asp
            645                 650                 655

Trp Leu Gly Cys
660

<210> SEQ ID NO 2
<211> LENGTH: 267
<212> TYPE: PRT
<213> ORGANISM: Homo sapiens

<400> SEQUENCE: 2

Met Arg Leu Thr Val Leu Cys Ala Val Cys Leu Leu Pro Gly Ser Leu
1               5                   10                  15

Ala Leu Pro Leu Pro Gln Glu Ala Gly Gly Met Ser Glu Leu Gln Trp
            20                  25                  30

Glu Gln Ala Gln Asp Tyr Leu Lys Arg Phe Tyr Leu Tyr Asp Ser Glu
        35                  40                  45

Thr Lys Asn Ala Asn Ser Leu Glu Ala Lys Leu Lys Glu Met Gln Lys
    50                  55                  60

Phe Phe Gly Leu Pro Ile Thr Gly Met Leu Asn Ser Arg Val Ile Glu
65                  70                  75                  80
```

```
Ile Met Gln Lys Pro Arg Cys Gly Val Pro Asp Val Ala Glu Tyr Ser
                85                  90                  95

Leu Phe Pro Asn Ser Pro Lys Trp Thr Ser Lys Val Val Thr Tyr Arg
            100                 105                 110

Ile Val Ser Tyr Thr Arg Asp Leu Pro His Ile Thr Val Asp Arg Leu
        115                 120                 125

Val Ser Lys Ala Leu Asn Met Trp Gly Lys Glu Ile Pro Leu His Phe
130                 135                 140

Arg Lys Val Val Trp Gly Thr Ala Asp Ile Met Ile Gly Phe Ala Arg
145                 150                 155                 160

Gly Ala His Gly Asp Ser Tyr Pro Phe Asp Gly Pro Gly Asn Thr Leu
                165                 170                 175

Ala His Ala Phe Ala Pro Gly Thr Gly Leu Gly Gly Asp Ala His Phe
            180                 185                 190

Asp Glu Asp Glu Arg Trp Thr Asp Gly Ser Ser Leu Gly Ile Asn Phe
        195                 200                 205

Leu Tyr Ala Ala Thr His Glu Leu Gly His Ser Leu Gly Met Gly His
210                 215                 220

Ser Ser Asp Pro Asn Ala Val Met Tyr Pro Thr Tyr Gly Asn Gly Asp
225                 230                 235                 240

Pro Gln Asn Phe Lys Leu Ser Gln Asp Asp Ile Lys Gly Ile Gln Lys
                245                 250                 255

Leu Tyr Gly Lys Arg Ser Asn Ser Arg Lys Lys
            260                 265

<210> SEQ ID NO 3
<211> LENGTH: 467
<212> TYPE: PRT
<213> ORGANISM: Homo sapiens

<400> SEQUENCE: 3

Met Phe Ser Leu Lys Thr Leu Pro Phe Leu Leu Leu Leu His Val Gln
1               5                   10                  15

Ile Ser Lys Ala Phe Pro Val Ser Ser Lys Glu Lys Asn Thr Lys Thr
                20                  25                  30

Val Gln Asp Tyr Leu Glu Lys Phe Tyr Gln Leu Pro Ser Asn Gln Tyr
            35                  40                  45

Gln Ser Thr Arg Lys Asn Gly Thr Asn Val Ile Val Glu Lys Leu Lys
        50                  55                  60

Glu Met Gln Arg Phe Phe Gly Leu Asn Val Thr Gly Lys Pro Asn Glu
65                  70                  75                  80

Glu Thr Leu Asp Met Met Lys Lys Pro Arg Cys Gly Val Pro Asp Ser
                85                  90                  95

Gly Gly Phe Met Leu Thr Pro Gly Asn Pro Lys Trp Glu Arg Thr Asn
            100                 105                 110

Leu Thr Tyr Arg Ile Arg Asn Tyr Thr Pro Gln Leu Ser Glu Ala Glu
        115                 120                 125

Val Glu Arg Ala Ile Lys Asp Ala Phe Glu Leu Trp Ser Val Ala Ser
130                 135                 140

Pro Leu Ile Phe Thr Arg Ile Ser Gln Gly Glu Ala Asp Ile Asn Ile
145                 150                 155                 160

Ala Phe Tyr Gln Arg Asp His Gly Asp Asn Ser Pro Phe Asp Gly Pro
                165                 170                 175

Asn Gly Ile Leu Ala His Ala Phe Gln Pro Gly Gln Gly Ile Gly Gly
            180                 185                 190
```

-continued

```
Asp Ala His Phe Asp Ala Glu Glu Thr Trp Thr Asn Thr Ser Ala Asn
        195                 200                 205

Tyr Asn Leu Phe Leu Val Ala His Glu Phe Gly His Ser Leu Gly
    210                 215                 220

Leu Ala His Ser Ser Asp Pro Gly Ala Leu Met Tyr Pro Asn Tyr Ala
225                 230                 235                 240

Phe Arg Glu Thr Ser Asn Tyr Ser Leu Pro Gln Asp Ile Asp Gly
                245                 250                 255

Ile Gln Ala Ile Tyr Gly Leu Ser Ser Asn Pro Ile Gln Pro Thr Gly
                260                 265                 270

Pro Ser Thr Pro Lys Pro Cys Asp Pro Ser Leu Thr Phe Asp Ala Ile
    275                 280                 285

Thr Thr Leu Arg Gly Glu Ile Leu Phe Phe Lys Asp Arg Tyr Phe Trp
    290                 295                 300

Arg Arg His Pro Gln Leu Gln Arg Val Glu Met Asn Phe Ile Ser Leu
305                 310                 315                 320

Phe Trp Pro Ser Leu Pro Thr Gly Ile Gln Ala Ala Tyr Glu Asp Phe
                325                 330                 335

Asp Arg Asp Leu Ile Phe Leu Phe Lys Gly Asn Gln Tyr Trp Ala Leu
            340                 345                 350

Ser Gly Tyr Asp Ile Leu Gln Gly Tyr Pro Lys Asp Ile Ser Asn Tyr
        355                 360                 365

Gly Phe Pro Ser Ser Val Gln Ala Ile Asp Ala Ala Val Phe Tyr Arg
    370                 375                 380

Ser Lys Thr Tyr Phe Phe Val Asn Asp Gln Phe Trp Arg Tyr Asp Asn
385                 390                 395                 400

Gln Arg Gln Phe Met Glu Pro Gly Tyr Pro Lys Ser Ile Ser Gly Ala
                405                 410                 415

Phe Pro Gly Ile Glu Ser Lys Val Asp Ala Val Phe Gln Gln Glu His
            420                 425                 430

Phe Phe His Val Phe Ser Gly Pro Arg Tyr Tyr Ala Phe Asp Leu Ile
        435                 440                 445

Ala Gln Arg Val Thr Arg Val Ala Arg Gly Asn Lys Trp Leu Asn Cys
    450                 455                 460

Arg Tyr Gly
465

<210> SEQ ID NO 4
<211> LENGTH: 707
<212> TYPE: PRT
<213> ORGANISM: Homo sapiens

<400> SEQUENCE: 4

Met Ser Leu Trp Gln Pro Leu Val Leu Val Leu Leu Val Leu Gly Cys
1               5                   10                  15

Cys Phe Ala Ala Pro Arg Gln Arg Gln Ser Thr Leu Val Leu Phe Pro
                20                  25                  30

Gly Asp Leu Arg Thr Asn Leu Thr Asp Arg Gln Leu Ala Glu Glu Tyr
            35                  40                  45

Leu Tyr Arg Tyr Gly Tyr Thr Arg Val Ala Glu Met Arg Gly Glu Ser
        50                  55                  60

Lys Ser Leu Gly Pro Ala Leu Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95
```

```
Pro Arg Cys Gly Val Pro Asp Leu Gly Arg Phe Gln Thr Phe Glu Gly
            100                 105                 110

Asp Leu Lys Trp His His His Asn Ile Thr Tyr Trp Ile Gln Asn Tyr
            115                 120                 125

Ser Glu Asp Leu Pro Arg Ala Val Ile Asp Asp Ala Phe Ala Arg Ala
130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Asp Glu
            195                 200                 205

Leu Trp Ser Leu Gly Lys Gly Val Val Pro Thr Arg Phe Gly Asn
210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
                260                 265                 270

Ser Glu Arg Leu Tyr Thr Gln Asp Gly Asn Ala Asp Gly Lys Pro Cys
            275                 280                 285

Gln Phe Pro Phe Ile Phe Gln Gly Gln Ser Tyr Ser Ala Cys Thr Thr
290                 295                 300

Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
                340                 345                 350

Phe Leu Gly Lys Glu Tyr Ser Thr Cys Thr Ser Glu Gly Arg Gly Asp
            355                 360                 365

Gly Arg Leu Trp Cys Ala Thr Thr Ser Asn Phe Asp Ser Asp Lys Lys
370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Met Tyr Arg Phe Thr Glu Gly Pro Pro Leu His
            420                 425                 430

Lys Asp Asp Val Asn Gly Ile Arg His Leu Tyr Gly Pro Arg Pro Glu
            435                 440                 445

Pro Glu Pro Arg Pro Thr Thr Thr Thr Pro Gln Pro Thr Ala Pro
            450                 455                 460

Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
                485                 490                 495

Pro Thr Ala Gly Pro Ser Thr Ala Thr Thr Val Pro Leu Ser Pro Val
            500                 505                 510

Asp Asp Ala Cys Asn Val Asn Ile Phe Asp Ala Ile Ala Glu Ile Gly
            515                 520                 525
```

-continued

```
Asn Gln Leu Tyr Leu Phe Lys Asp Gly Lys Tyr Trp Arg Phe Ser Glu
        530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Pro Leu Ser
            565                 570                 575

Lys Lys Leu Phe Phe Phe Ser Gly Arg Gln Val Trp Val Tyr Thr Gly
            580                 585                 590

Ala Ser Val Leu Gly Pro Arg Arg Leu Asp Lys Leu Gly Leu Gly Ala
        595                 600                 605

Asp Val Ala Gln Val Thr Gly Ala Leu Arg Ser Gly Arg Gly Lys Met
    610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
            660                 665                 670

Phe Cys Gln Asp Arg Phe Tyr Trp Arg Val Ser Ser Arg Ser Glu Leu
        675                 680                 685

Asn Gln Val Asp Gln Val Gly Tyr Val Thr Tyr Asp Ile Leu Gln Cys
    690                 695                 700

Pro Glu Asp
705
```